(12) United States Patent
Shchory et al.

(10) Patent No.: US 8,193,508 B2
(45) Date of Patent: Jun. 5, 2012

(54) DETECTING PHOTONS IN THE PRESENCE OF A PULSED RADIATION BEAM

(75) Inventors: Tal Shchory, Kibbutz Ranat Menashe (IL); Giora Kornblau, Binyamina (IL); David Maier Neustadter, Nof Ayalon (IL); Saul Stokar, Raanana (IL)

(73) Assignee: Navotek Medical Ltd., Yokneam (IL)

( * ) Notice: Subject to any disclaimer, the term of this patent is extended or adjusted under 35 U.S.C. 154(b) by 0 days.

(21) Appl. No.: 12/746,348

(22) PCT Filed: Dec. 4, 2008

(86) PCT No.: PCT/IL2008/001575
§ 371 (c)(1),
(2), (4) Date: Sep. 7, 2010

(87) PCT Pub. No.: WO2009/072124
PCT Pub. Date: Jun. 11, 2009

(65) Prior Publication Data
US 2011/0006212 A1    Jan. 13, 2011

Related U.S. Application Data

(60) Provisional application No. 60/992,691, filed on Dec. 5, 2007.

(51) Int. Cl.
*G21K 1/02* (2006.01)
(52) U.S. Cl. .................................................. 250/363.1
(58) Field of Classification Search .. 250/363.01–363.1, 250/492.1–492.2, 393, 395; 378/4, 64, 65, 378/8, 95; 600/1, 426, 427
See application file for complete search history.

(56) References Cited

U.S. PATENT DOCUMENTS
5,233,990 A    8/1993    Barnea
(Continued)

FOREIGN PATENT DOCUMENTS
EP    1 419 799 A1    5/2004
(Continued)

OTHER PUBLICATIONS

International Search Report from the European Patent Office in International Application No. PCT/IL2008/001575 mailed Apr. 21, 2009.
(Continued)

*Primary Examiner* — Kiho Kim
(74) *Attorney, Agent, or Firm* — Finnegan, Henderson, Farabow, Garrett & Dunner, L.L.P.

(57) ABSTRACT

A detector system adapted for monitoring a radiation treatment system comprising a pulsed beam radiation source for treating a body with a given beam intensity and beam configuration, with pulse times and intervals between pulses less than 100 milliseconds, using at least one monitoring radiation source located inside or outside the body, the detector system comprising; a) a detector designed to detect radiation from the monitoring source, and subject to interference radiation from the beam source; and b) control circuitry that creates a data record of radiation received by the detector, to provide information about the body; wherein, when the detector detects radiation in real time during operation of the beam, the data record selectively excludes data for radiation received by the detector during the pulses, as opposed to data for radiation received by the detector between pulses.

34 Claims, 4 Drawing Sheets

U.S. PATENT DOCUMENTS

| | | | |
|---|---|---|---|
| 6,118,848 A * | 9/2000 | Reiffel | 378/65 |
| 6,405,072 B1 | 6/2002 | Cosman | |
| 6,618,467 B1 | 9/2003 | Ruchala et al. | |
| 6,662,036 B2 | 12/2003 | Cosman | |
| 6,683,318 B1 | 1/2004 | Haberer et al. | |
| 6,804,548 B2 | 10/2004 | Takahashi et al. | |
| 6,839,404 B2 | 1/2005 | Clark et al. | |
| 6,865,411 B2 | 3/2005 | Erbel et al. | |
| 7,171,257 B2 | 1/2007 | Thomson | |
| 7,263,164 B2 | 8/2007 | Ghelmansarai et al. | |
| 7,295,648 B2 | 11/2007 | Brown | |
| 7,302,033 B2 | 11/2007 | Carrano et al. | |
| 7,349,522 B2 | 3/2008 | Yan et al. | |
| 7,438,685 B2 | 10/2008 | Burdette et al. | |
| 2005/0080332 A1 | 4/2005 | Shiu et al. | |
| 2005/0197564 A1 | 9/2005 | Dempsey | |
| 2007/0016014 A1 | 1/2007 | Hara et al. | |
| 2007/0153969 A1 | 7/2007 | Maschke | |
| 2008/0130825 A1 | 6/2008 | Fu et al. | |
| 2008/0260099 A1 | 10/2008 | Pfeiler | |

FOREIGN PATENT DOCUMENTS

| | | |
|---|---|---|
| EP | 1 419 801 A1 | 5/2004 |
| WO | WO 99/35966 | 7/1999 |
| WO | WO 02/22210 A1 | 3/2002 |
| WO | WO 2004/033027 A2 | 4/2004 |
| WO | WO 2007/017847 A1 | 2/2007 |

OTHER PUBLICATIONS

Written Opinion of the International Searching Authority dated Jun. 8, 2010 for PCT application No. PCT/IL2008/001575 (12 pages).

Office Action dated Aug. 15, 2011 issued by the Israel Office for Patent Application No. 206178 (5 pages total: including 2 pages original document; 3 pages English language translation including translations of the Israel Patent Law).

Ipe, N. Answer to Question #4511 Submitted to "Ask the Experts", *Health Physics Society*, available from http://hps.org/publicinformation/ate/q4511.html (answer indicated as posted May 17, 2005) (2 pages).

Crespo, P. et al., "First In-Beam PET Imaging With LSO/APD Array Detectors" *IEEE Transactions On Nuclear Science*, vol. 51, No. 5, Oct. 2004 (8 pages).

McCall, R. C. et al., "The Response of Survey Meters to Pulsed Radiation Fields", SLAC-PUB-4488, Nov. 1987 (available from www.slac.stanford.edu/cgi-wrap/getdoc/slac-pub-4488.pdf) (4 pages).

Parodi, K. et al., "The Time Dependence of the γ-Ray Intensity Seen by an In-Beam PET Monitor," in *Annual Report 2002: Institute of Nuclear and Hadron Physics*, Eds. F. Dönau et al., p. 77, May 2003 (available from www.fzd.de/FWK/jb02/PDF/page77.pdf) (1 page).

Peters, A. et al., "Spill Structure Measurements at the Heidelberg Ion Therapy Centre", Proceedings of EPAC'08, Genoa, Italy, pp. 1824-26, Jul. 2008 (available from epaper.kek.jp/e08/papers/tupp127.pdf) (3 pages).

Pshenichnov, I. et al., "PET Monitoring of Cancer Therapy with $^3$HE and $^{12}$C Beams: A Study With the GEANT4 Toolkit", dated Aug. 13, 2007, submitted to Phys. Med. Biol. (available from arxiv.org/PS_cache/arxiv/pdf/0708/0708.1691v1.pdf) (19 pages).

* cited by examiner

DETECTING PHOTONS IN THE PRESENCE OF A PULSED RADIATION BEAM

RELATED APPLICATIONS

This application claims benefit under 35 USC 119(e) from U.S. provisional patent application 60/992,691, filed on Dec. 5, 2007.

The contents of all of the above documents are incorporated by reference as if fully set forth herein.

FIELD AND BACKGROUND OF THE INVENTION

The present invention, in some embodiments thereof, relates to radiation detection systems used in the vicinity of pulsed radiation beams and other radiation sources; and, more particularly, but not exclusively, to x-ray and gamma-ray imaging and tracking systems used to monitor patients while they are treated by pulsed radiation therapy beams.

Radiation therapy is often used to treat cancer and other abnormal growths. Such therapy can use implanted radioactive sources (brachytherapy), or external radiation sources, generally beams, including x-ray beams and electron beams produced by linacs, as well as proton beams and heavy ion beams. Such beams are also used for radiosurgery, for example for ablating cardiac tissue to prevent atrial fibrillation. Because radiation beams can harm healthy tissue, radiation beam therapy and radiosurgery are carefully planned, with beams aimed precisely at a target such as a tumor, often with several doses of radiation given from different angles, to make sure that the target receives enough radiation, while minimizing the exposure of healthy tissue to radiation.

U.S. Pat. No. 6,683,318 to Haberer et al describes a heavy ion beam therapy system, in which positron emission tomography (PET) is used to locate radioactive nuclei that decay by positron emission, produced in the target tissue by the heavy ion beam. The PET results can verify that the heavy ion beam was aimed properly. In order to locate these positron-emitting nuclei before they have moved away from the target, PET is performed during the treatment session. The most convenient time for doing this is said to be in the time slots between beam spills, when the PET signal is less obscured by background noise than in the periods with the beam on. As defined in other publications by the inventors and their research group at Darmstadt, "beam spills" refers to periods of one to five seconds during which the beam is on, separated by time slots of similar length during which the beam is off. This use of "beam spill" is found, for example, in Parodi et al, "The Time Dependence of the γ-Ray Intensity Seen by an In-Beam PET Monitor," downloaded from www.fzd.de/FWK/jb02/PDF/page77.pdf, on Nov. 23, 2008; Peters et al, "Spill Structure Measurements at the Heidelberg Ion Therapy Centre," Proceedings of EPAC08, Genoa, Italy, paper TUPP127, pages 1824-1826, downloaded from epaper.kek.jp/e08/papers/tupp127.pdf, on Nov. 23, 2008; Crespo et al, "First In-Beam PET Imaging With LSO/APD Array Detectors," IEEE Trans. Nucl. Sci. 15, 2654-2661 (2004); and Pshenichnov et al, "PET monitoring of cancer therapy with $^3$He and $^{12}$C beams: a study with the GEANT4 toolkit," submitted to Phys. Med. Biol., downloaded from arxiv.org/PS_cache/arxiv/pdf/0708/0708.1691v1.pdf, on Nov. 23, 2008.

U.S. Pat. Nos. 7,438,685 and 6,804,548 describe using ultrasound to monitor the position of a target organ or tumor in real time during beam therapy. US 2005/0197564 to Dempsey describes using real time MRI during beam therapy.

U.S. Pat. No. 7,349,522 describes software for simulating dynamic radiation therapy, for example gated to respiration, using fluoroscope images fused to previously acquired reference images. But they do not suggest the use of such fluoroscope images during actual beam therapy, instead using index markers or other known methods of gating to respiration.

U.S. Pat. No. 7,302,033 describes real time "image guided radiation treatment," using a linac for treatment, and a stereo x-ray system for real time imaging, arranged so neither one blocks the other. "Real time" is defined to mean anytime during a treatment delivery phase, with the linac turned on or off. Specifically, they describe making an x-ray image before turning on the linac, delivering a dose of radiation with the linac, then making another image with the linac turned off, delivering another dose of radiation, etc.

US 2008/0130825 to Fu et al describes using image guided radiation therapy, including x-ray imaging, while the beam is turned on or off. Image segmentation is used in real time to better identify the target, for example a tumor.

US 2005/0080332 to Shiu describes using "near simultaneous" CT image guided radiotherapy.

U.S. Pat. No. 7,295,648 describes using linac x-rays for imaging "by suitable variation of the output energy". U.S. Pat. No. 5,233,990 describes using a lower energy therapeutic x-ray beam, from an x-ray tube, for imaging in real time, to verify the position of the patient. U.S. Pat. No. 6,839,404 describes using linac x-rays for imaging before delivering a dose of x-rays for therapy, and using the detector to monitor the dose during therapy. U.S. Pat. No. 6,618,467 describes using linac x-rays to produce CT images in real time. Because the therapy x-rays do not make up a complete set of angles for CT, they supplement them with low level x-rays at other angles, obtained from leakage through the shutters of the linac, or from sources other than the linac, collected either before or during treatment. They also describe using only the low level x-rays to produce the CT images.

U.S. Pat. No. 7,263,164 describes using an x-ray imaging system in real time, during treatment by a linac beam. Scattering from the linac beam into the detector is estimated, using a phantom, and subtracted from the image.

U.S. Pat. No. 7,171,257 describes doing x-ray imaging just before radiosurgery, finding the change in position of the beam target, for example cardiac tissue to be ablated, as a function of cardiac phase and breathing phase, then using that information, with the imaging system turned off, to keep the beam aimed correctly during the radiosurgery, monitoring the breathing and cardiac cycles in real time.

U.S. Pat. No. 6,865,411 states that it is a disadvantage that imaging and radiation beam therapy cannot be done at the same time.

U.S. Pat. No. 6,662,036 and U.S. Pat. No. 6,405,072 describe using index markers to track movement of the patient in real time, during beam therapy.

"Answer to Question #4511 Submitted to 'Ask the Experts'" on the Health Physics Society website, downloaded on Nov. 27, 2008 from hps.org/publicinformation/ate/q4511.html, states that most medical linacs are pulsed with repetition rates of 100 to 400 pulses per second, and pulse lengths of 1 to 10 microseconds, resulting in a very low duty cycle, less than 1% or less than 0.1%, and peak intensities of radiation much higher than the average intensity. Radiation detectors that have long dead times, such as Geiger-Muller and proportional counters, tend to become saturated at such high peak intensities, and are not suitable for safety monitoring of radiation levels outside rooms where linacs are used. Similar points are made by R. McCall and N. Ipe, "The Response of Survey Meters to Pulsed Radiation Fields,"

SLAC-PUB-4488 (1987), downloaded from www.slac.stanford.edu/cgi-wrap/getdoc/slac-pub-4488.pdf, on Nov. 27, 2008.

*Radiation Detection and Measurement* by Glenn Knoll, 3rd edition (2000), ISBN 0-471-07338-5, describes instruments for detecting x-ray and gamma-ray photons.

SUMMARY OF THE INVENTION

An aspect of some embodiments of the invention concerns a system for treating a body with a pulsed beam of ionizing radiation, for example a radiation therapy beam, while using a detector system to obtain data of the body being treated, from another ionizing radiation source such as an x-ray or gamma-ray imaging or tracking system, in real time during operation of the beam. The detection system reduces or avoids interference from the beam, by not recording data and/or by having reduced sensitivity during the pulses of the beam, while using the intervals between pulses to obtain the data.

There is thus provided, in accordance with an exemplary embodiment of the invention, a detector system adapted for monitoring a radiation treatment system comprising a pulsed beam radiation source for treating a body with a given beam intensity and beam configuration, with pulse times and intervals between pulses less than 100 milliseconds, using at least one monitoring radiation source located inside or outside the body, the detector system comprising:
  a) a detector designed to detect radiation from the monitoring source, and subject to interference radiation from the beam source; and
  b) control circuitry that creates a data record of radiation received by the detector, to provide information about the body;
wherein, when the detector detects radiation in real time during operation of the beam, the data record selectively excludes data for radiation received by the detector during the pulses, as opposed to data for radiation received by the detector between pulses.

Optionally, the detector sensitivity is controllable by the control circuitry, and the data record selectively excludes data for radiation received during the pulses because the detector system is configured to make the sensitivity of the detector lower during the pulses than between the pulses.

Optionally, the detector has a bias voltage, and the control circuitry makes the sensitivity of the detector lower by changing the bias voltage.

In an embodiment of the invention, the data record selectively excludes data for radiation received during the pulses because the control circuitry is configured not to add data for radiation detected during the pulses to the data record.

Optionally, the detector system uses a triggering element that signals the timing of the pulses to the control circuitry.

Optionally, the triggering element is comprised in the beam source, or in a timing element that controls the timing of the beam pulses.

Alternatively, the triggering element is comprised in a sensor which senses when the beam source produces a pulse.

Optionally, the sensor is the detector.

Optionally, the data record selectively excludes data for radiation received during the pulses because the control circuitry is configured to remove said data from the data record data.

In an embodiment of the invention, the data record selectively excludes data for radiation received during the pulses because the detector is configured to saturate at a level of radiation received during the pulses at the given beam intensity and beam configuration, but not to saturate at a level of radiation received from the monitoring source between pulses.

Optionally, the detector is a scintillation detector with decay time shorter than the intervals between pulses.

Optionally, the time-averaged relative contribution of the interference to the data record is less, by at least a factor of 5, than the time-averaged relative contribution of the interference to the radiation received by the detector, when the beam is operating at the given beam intensity and beam configuration.

Optionally, the interference contributes to the data record less than 20% as much as the radiation from the monitoring source, averaged over any time interval that includes many pulses, when the beam is operating at the given beam intensity and beam configuration.

In an embodiment of the invention, the radiation treatment system that the detector system is adapted for monitoring is a radiation therapy system using a beam intensity of at least 1 centiGray per second, and the detector system can locate a beam therapy target inside the patient to within 2 mm in an acquisition time of less than 2 seconds, using an internal monitoring source of less than 1 milliCurie or an external x-ray monitoring source of less than 20 centiGray per acquisition time.

Optionally, the data record provides information on one or more of motion of the patient's body, position of the patient's body, motion and position of one or more parts of the patient's body, all relative to the beam in real time when the beam is on, and a dose of radiation received from the beam by one or more parts of the patient's body.

Optionally, the pulsed beam source in the radiation treatment system that the detector system is adapted to monitor comprises a linac beam source.

Optionally, the linac beam source comprises an x-ray beam source.

Alternatively, the pulsed beam source in the radiation treatment system that the detector system is adapted to monitor comprises an ion beam source.

In an embodiment of the invention, the detector system comprises an x-ray imaging system, using a monitoring source comprising an x-ray source.

Optionally, the detector system comprises a CT system.

Alternatively or additionally, the detector system comprises a radioactive tracking system, using a monitoring source comprising a radioactive source inside the body being treated.

Alternatively or additionally, the detector system comprises a gamma imaging system, using a monitoring source comprising radioactive material inside the body being treated.

Optionally, the control circuitry is adapted to determine a difference between a position of a treatment target in the body and planned position with respect to the beam, and to adjust a position of the beam and/or reduce the power of the beam in response to the difference.

Optionally, the control circuitry is fast enough, or the detector has a fast enough decay time, or both, so that the data record can selectively exclude data for radiation received by the detector during a time period shorter than 100 milliseconds, as opposed to data for radiation received by the detector outside the time period.

Optionally, the time period is shorter than 10 milliseconds.

There is further provided, in accordance with an exemplary embodiment of the invention, a method of monitoring a body in real time while the body is being treated by a pulsed beam of treatment radiation, with pulse lengths and interval between pulses both shorter than 100 milliseconds, the method comprising:

a) passing monitoring radiation from a source other than the beam through at least part of the body;

b) receiving the monitoring radiation together with any interfering radiation from the beam, and detecting and recording at least some of the radiation in a data record;

c) using the data record to monitor the body in real time during the treatment;

wherein detecting and recording the radiation selectively excludes from the data record data for radiation received during the beam pulses.

Optionally, using the data record to monitor comprises reconstructing images.

Optionally, the monitoring radiation comes from a source inside the body, and using the data record to monitor comprises tracking a location of the source.

Optionally, the body is a patient's body, and the treatment by the beam comprises radiation therapy on the patient.

Optionally, recording the radiation comprises selectively failing to record, or selectively removing from the data record, data for radiation detected during the beam pulses.

Optionally, the method also includes lowering a detection sensitivity to radiation during the beam pulses, and raising the detection sensitivity during intervals between pulses.

Optionally, the method also includes receiving triggering signals indicating the beginning and end of each pulse, wherein lowering and raising the detection sensitivity is done in response to the triggering signals.

Optionally, detecting the radiation comprises detecting with a saturation level lower than a level of radiation received during the beam pulses, but higher than a level of radiation received during intervals between the beam pulses.

Optionally, using the data record to monitor in real time comprises:

a) determining a difference between a position of a beam therapy target in the patient, and a planned position with respect to the beam; and b) adjusting a position of the beam, and/or reducing the power of the beam, in response to the difference.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Figure 1:
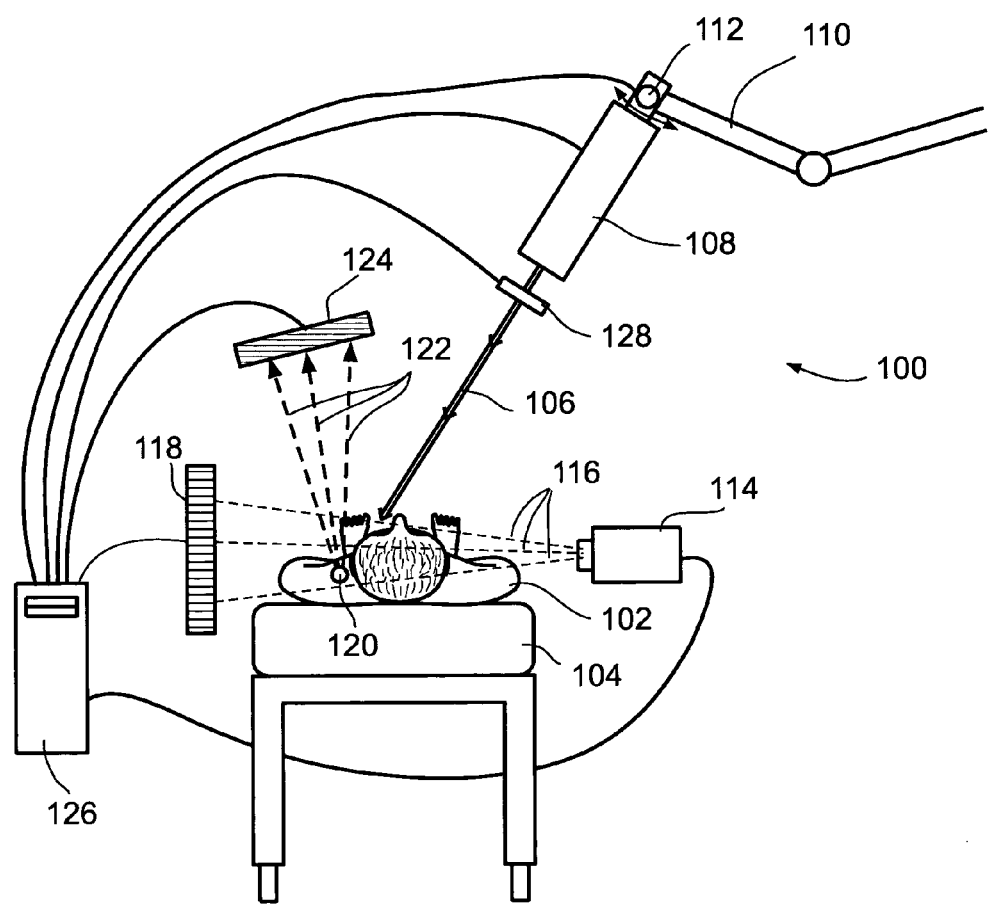
FIG. 1 schematically shows a radiation treatment system according to an exemplary embodiment of the invention.

The present invention, in some embodiments thereof, relates to radiation detection systems used in the vicinity of pulsed radiation beams and other radiation sources, and, more particularly, but not exclusively, to x-ray and gamma-ray imaging and tracking systems used to monitor patients while they are treated by pulsed radiation therapy beams.

An aspect of some embodiments of the invention concerns a radiation treatment system that uses a pulsed beam of radiation to treat a body, with pulse lengths and intervals between pulses shorter than 100 milliseconds, together with a detector system that uses another source of radiation to monitor the body during the treatment. In an exemplary embodiment of the invention, the detector system reduces or avoids interference from the beam by having reduced sensitivity during the pulses, or not recording data for radiation detected during the pulses, and recording data for radiation detected in the intervals between pulses.

Optionally, the sensitivity of the detector is decreased by lowering a bias voltage used by the detector, triggered, for example, by a sensor that responds to the beam pulses, or triggered by the increased intensity of radiation that the detector measures just as a pulse is beginning. Alternatively or additionally, the detector has a lower sensitivity during the beam pulses because the detector saturates at a level well below the intensity of radiation it receives during the beam pulses, but optionally at a higher level than the highest intensity of radiation expected from the other source of radiation. The detector may be paralyzed when it saturates, not responding at all, or non-paralyzed, responding at a maximum rate, or something in between these two extremes. Additionally or alternatively, any radiation detected during the beam pulses is removed, for example by software, from a data record of the detector, with the beam pulses optionally identified by the higher levels of radiation detected by the detector then.

Optionally, the beam of radiation is a radiation therapy beam, for example a linac-generated x-ray beam or electron beam, or an ion beam, used to treat a patient, and the detector system monitors the patient in real time during the therapy, for example to determine the position of the patient's body, or of parts of the body, and to detect any change in their position, and optionally adjust the aim of the beam in response. Additionally or alternatively, the detector system monitors the patient in real time, in order to accurately determine the dose of radiation delivered to a desired target in the patient's body, for example a tumor, and/or the dose of radiation delivered to healthy tissue, and optionally adjust the beam intensity and/or the beam path. Optionally, the detector system is an x-ray or gamma-ray imaging or tracking system, and the other source of radiation is an x-ray source such as an x-ray tube, or a radioactive marker or other radioactive material in the patient's body.

Before explaining at least one embodiment of the invention in detail, it is to be understood that the invention is not necessarily limited in its application to the details set forth in the following description. The invention is capable of other embodiments or of being practiced or carried out in various ways.

Referring now to the drawings, FIG. 1 illustrates a radiation treatment system 100, with detector systems for monitoring using separate monitoring radiation sources, according to an exemplary embodiment of the invention. A patient 102, lying on a bed or table 104, is being treated by a radiation therapy beam 106 generated by a pulsed beam source 108, for example a linac producing hard x-rays for treating cancer. Alternatively, the pulsed beam source is a linac producing an electron beam, or a proton beam source, or a heavy ion beam source, or any other kind of pulsed beam source used for radiation therapy. The pulses, which typically each last for 1 to 10 microseconds, generally occur at regular intervals shorter than 100 milliseconds, typically at intervals between 2.5 and 10 milliseconds, when the beam is on, and typically the beam is on for 1 to 20 seconds at a time. In some linacs, certain pulses may be missing, in some pattern, to adjust the dose rate, so the pulses will not all occur at fixed intervals, but in a more complicated pattern. As used herein, the beam is said to be "on" or "operating" or "treating the patient" when it is producing pulses at one of its normal rates and patterns, including during the intervals between pulses, and is said to be "off" or "pausing" when it is not generating pulses at all. The beam source operates the beam at a given beam intensity and beam configuration, including beam diameter, spread, energy distribution and composition, appropriate for radiation therapy, and characteristics of the monitoring detector systems may be adjusted depending on the beam intensity and beam configuration. Optionally, beam source 108 is mounted on an arm or gantry 110, with a control 112 for adjusting the direction and/or position of the beam. Optionally, there is a detector system using another radiation source 114, for example an x-ray tube, producing radiation 116, which is detected by detector 118, for imaging patient 102 in real time, for monitoring during radiation treatment. In a prior art radiation treatment system with a linac beam and a radiation detector operating at the same time, photons, electrons, and emitted neutrons from the beam would enter the detector directly, or after scattering from the patient or other objects in the room, and cause substantial interference in data generated by the detector. But for reasons that will be explained below, the data generated by detector 118 suffers from relatively little interference from beam 106. Additionally or alternatively, there is a detector system using an internal radioactive source 120 in the patient, for example an implanted compact marker, or extended radioactive material, injected or ingested to mark the location of a tumor or other target being treated by beam 106, which emits radiation 122, for example gamma rays, which are detected by a detector 124. In some embodiments of the invention, radioactive source 120 is generated inside the patient's body by the beam, for example it is a positron source generated by spallation of a heavy ion beam. The data generated by detector 124 also has relatively little interference from beam 106, for reasons that will be explained. Detector 124 is, for example, a gamma camera, or a radioactive tracker, used to image or track the radioactive marker or material in the patient's body, in real time, for monitoring during the beam treatment.

A controller 126, for example a computer, optionally reconstructs images of patient 102 and/or source 120, and/or tracks the position of source 120, using data generated by detectors 118 and/or 124, and detects any changes in position of the patient or of internal tissues or organs being targeted by the beam, in real time. An image can be reconstructed, for example, from measurements of the absorption of x-rays on different chords going through the body, forming a 2-D x-ray image. Alternatively, instead of reconstructing an image, a compact radioactive source in the body, generally a gamma-ray source, can be tracked, for example by using three differential detectors to determine the position of its center of mass in each of three dimensions, and then following changes in the position, as described for example in WO 2006/016368 and WO 2007/017846, both assigned to Navotek Medical Ltd. A 2-D image can also be reconstructed by a gamma camera, scanning a detector over the body to measure a spatial distribution of a gamma-ray emitting radioactive material in the body, but x-ray imaging and gamma-ray tracking have the potential advantage that they are much faster, and may be better suited for finding changes in the position of a beam therapy target in real time.

This information is used by controller 126, either automatically or in conjunction with a human operator, to make any needed changes in the location or direction of the beam, using control 112 and arm 110, as well as possibly turning off beam source 108 in real time to avoid damaging healthy tissue, if beam 106 is no longer aimed properly, and leaving beam source 108 off until the aim of the beam and/or the position of the patient can be adjusted.

As used herein, each detector used for monitoring the patient using a given radiation source, for example detector 118 using source 114, or detector 124 using source 120, including any control circuitry, is referred to as a detector system. The control circuitry can be common to more than one detector system, as in the case of controller 126 in FIG. 1, or can be separate for one or more detector systems, packaged with the detector for example. As used herein, the control circuitry of a detector system includes any elements which create or modify data records; use data records for imaging or tracking; use results of the imaging or tracking for control, for example of the beam source; actively control the sensitivity or other characteristics of the detector; receive signals for actively controlling the detector, for example signals about the beginning and end of beam pulses. All of these functions of the control circuitry need not be present in a given detector system, and they may be performed by the same or different elements, packaged together or separately. A given detector system may use more than one radiation source, and a given source may be used by more than one detector system. The sources used by the detector systems, such as external source 114 and internal source 120, are referred to as monitoring sources, and their radiation referred to as monitoring radiation, to distinguish them from the beam source, and from the interfering radiation coming directly and indirectly from the beam.

To reduce or avoid interference from beam 106 when it is operating, controller 126 uses a data record with data from detectors 118 and/or 124, for imaging and tracking. The data record selectively excludes data for the radiation received during the pulses of beam 106, as opposed to data for radiation received between the pulses. Since interference from beam 106 occurs primarily during the pulses, from beam radiation hitting the detectors directly or after scattering, this selective exclusion decreases the effect of interference from beam 106 on the imaging or tracking. As used herein, "selectively excludes" does not necessarily mean that data is excluded for all radiation received during the beam pulses, but data is excluded for a greater proportion of such radiation, than for radiation received during the intervals between pulses. Optionally, data is excluded for most or all radiation received during the beam pulses. As used herein, excluding data can include not adding data to the data record because the radiation was not detected, not recording data to the data record even though the radiation was detected, and removing data from the data record after it was recorded. As used herein, "data record" can include any data from the detector used for imaging or tracking, even if the data is only kept in a computer memory and used continuously in real time for imaging or tracking, and never saved. As used herein, "interfering radiation" or "interference radiation" includes radiation directly entering a detector from the beam source, as well as radiation from the beam source which is scattered before entering the detector, or is absorbed and re-emitted in much less time than the time between pulses. It does not include radiation from activated nuclei or excited atoms which is emitted in a time that is not short compared to the time between pulses.

System 100 has a potential advantage over prior art systems in which a radiation beam is turned on to provide a dose of radiation to the patient, then paused for a few seconds or longer while the patient is imaged to see if he or she has moved, then turned on again, and the procedure repeated several times. In such a prior art system, the pauses in treatment to image the patient make the treatment session last longer, making the session more difficult for the patient, and resulting in lower throughput for the expensive beam therapy system. The longer treatment sessions also make it more likely that the patient will move. In addition, because the imaging is not done in real time, it is not possible to stop or adjust the beam if the patient moves in the middle of treatment, and one cannot be certain that the patient's position as measured after the treatment is exactly the same as the patient's position while the treatment was going on. In system 100, imaging may be done in real time during treatment, so there are no pauses in the treatment session, it is possible to stop or make adjustments in the beam as soon as the patient moves, and it is possible to verify that the beam was aimed properly during the treatment.

In some embodiments of the invention, decreasing the contribution to the data record of radiation received during the beam pulses is accomplished by actively making the detectors less sensitive during the pulses. For example, a sufficiently fast sensor 128 in the path of beam 106 senses the timing of the pulses, and communicates this information to controller 126, which decreases the sensitivity of the detectors, for example by lowering their bias voltage. Additionally or alternatively, information about the timing of the pulses may come directly from beam source 108.

In some embodiments of the invention, detectors 118 and/or 124 are not necessarily less sensitive to radiation during the pulses than in the intervals between the pulses, but the detectors, or controller 126, do not record data on any radiation received during the pulses, or controller 126 removes this data from a data record after it has been written.

In some embodiments of the invention, the detectors are less sensitive to radiation during the pulses because they have a saturation level that is much lower than the radiation level received during the pulses, primarily from the beam, but optionally the saturation level is higher than the radiation level received during the intervals between pulses, primarily from the other radiation sources 114 and/or 120. In those embodiments, controller 126 and detectors 118 and 124 do not need to use information about the timing of the pulses.

There are a variety of types of radiation detectors that are optionally used for detectors 118 and 124. These include rare earth screens, photostimulable phosphors, Geiger counters, proportional counters, scintillators, direct semiconductor detectors, and a combination of scintillators with semiconductor detectors (indirect detectors). These devices generally have a sensitivity that is controllable, for example by controlling a bias voltage, and/or a saturation level that is controllable, for example by controlling an integration time and a maximum recharging current. In principle even photographic plates or x-ray film could be used, with, for example, a shield with an aperture and a shutter than can be closed during the pulses, or a rotating shield with one or more openings that are timed to be closed during the pulses. But shielding that is effective against the hard x-rays typically used for radiation therapy, above 1 MeV, is generally quite massive, and devices whose sensitivity or saturation level can be controlled electronically have the potential advantage that it is not necessary to apply the high inertial forces that would be used to open and close a massive, high speed mechanical shutter, or to use the high rotational energy associated with a massive, rapidly rotating shield.

Detector 118 and/or 124 may be divided into a plurality of sections each corresponding to a pixel of an image, optionally with a collimator so that each section is sensitive primarily to radiation from a relatively narrow range of directions, and/or radiation that has passed through the body along a narrow range of paths. The detector may produce a single 1-D or 2-D image from radiation reaching the detector when the detector and source are at fixed position. Examples of such systems include x-ray imaging systems using an external x-ray tube, and gamma cameras, such as an Anger camera, using a distributed internal radioactive source.

Alternatively, the detector may be used to detect radiation with the detector at a series of different positions or orientation, and/or with the source, particularly an external source, at a series of different positions and orientations, to produce a 2-D or 3-D tomographic image. Systems producing tomographic images include CT (computerized tomography) systems using an external x-ray source, and SPECT (single photon emitted computer tomography) and PET (positron emission tomography) systems, using an internal radioactive source.

Alternatively, the detector may be used in a tracking system, to locate and track a compact radioactive source, or a plurality of compact sources, inside the body. Examples of such tracking systems, using gamma ray sources, are described, for example, in WO 2006/016368 and in WO 2007/017846, both assigned to Navotek Medical, Ltd.

Whether the detector is used for imaging or tracking or both, if the radiation treatment system is used for beam therapy of patients, as system 100 is, then the detector system optionally provides information that is useful for real-time monitoring of patients during beam therapy. For example, the detector system can find the position of a therapy target inside the patient's body, to within a precision, such as 2 mm or 1 mm, that is adequate for providing effective and safe aiming of the beam, in an acquisition time, such as 1 second or 2 seconds, that is short enough so that if an error in aiming is found, the beam can be adjusted or turned off without any significant harm done. This can be done using a medically safe monitoring radiation source, either a safe internal radioactive source, for example no more than 1 milliCurie, or no more than 100 microCuries, or a safe external x-ray source, for example no more than 20 centiGray per acquisition time, or no more than 2 centiGray, or no more than 0.2 centiGray. And it can be done even in the presence of an x-ray therapy beam as strong as 1 centiGray per second, or 3 centiGrays per second, or 10 centiGrays per second.

Certain characteristics of the detectors may be advantageous:

1) Short integration time. It is potential advantageous if the integration time of the detector is short compared to the length of a pulse, so that the detector sensitivity during a pulse can be lower than the detector sensitivity during the intervals between pulses. Alternatively, if the integration time is longer than or comparable to a pulse length but much shorter than the interval between pulses, then the detector sensitivity can be lower for several integration times around the pulse, still leaving most of the much longer interval between pulses during which the detector can have high sensitivity. For scintillation based detectors, the integration time depends on the decay time of the scintillation pulses, which may be defined as the time required for the scintillation pulse to fall to 1/e of its maximum value.

2) Low afterglow. Some detectors produce an afterglow for a period of time, for example a few milliseconds, after radiation is received by the detector. It is potentially advantageous if the afterglow is sufficiently low, or sufficiently short-lived, or both, so that the afterglow from radiation received during a pulse does not substantially interfere with the detection of radiation between pulses. Halide scintillation crystals, particularly thallium doped sodium iodide and thallium doped cesium iodide tend to exhibit long afterglow, as high as a few percent after 3 milliseconds. Cadmium tungstate ($CdWO_4$) crystals, bismuth germinate (BGO, or $Bi_4Ge_3O_{12}$), and zinc selenide (ZnSe) doped with oxygen or tellurium, are examples of low afterglow scintillation materials.

3) High radiation hardness. Because the detector is exposed to a relatively high level of radiation from the beam, it is potentially advantageous to use a detector with relatively high radiation hardness, for example a detector whose functioning will not be substantially affected after exposure to 10,000 gray. Examples of radiation hard scintillation materials include cadmium tungstate, gadolinium silicate ($Gd_2SiO_5$), and undoped cesium iodide. Alternatively, if the detector material is low enough in cost, it can be replaced when it is damaged by radiation.

4) Low neutron activation. X-rays from a linac, particularly x-ray of energy 10 MeV or greater, can release neutrons from nuclei from material exposed to the beam, and these neutrons can activate materials in the vicinity of the beam, including detectors 118 and 124. The resulting radioactive isotopes can interfere with the detectors, producing spurious data. Since most radioactive isotopes that are of concern have half-lives much longer than the typical time intervals between pulses, this source of interference cannot be avoided by making the detector less sensitive during pulse times. It is optionally minimized by using detector materials with low neutron activation levels, and/or by using a linac beam with energy below 10 MeV, so that few neutrons will be released. It is potentially advantageous to avoid the use of gold and silver, which have high neutron activation levels, and to use molybdenum and tungsten, which have low neutron activation levels.

Figure 2:
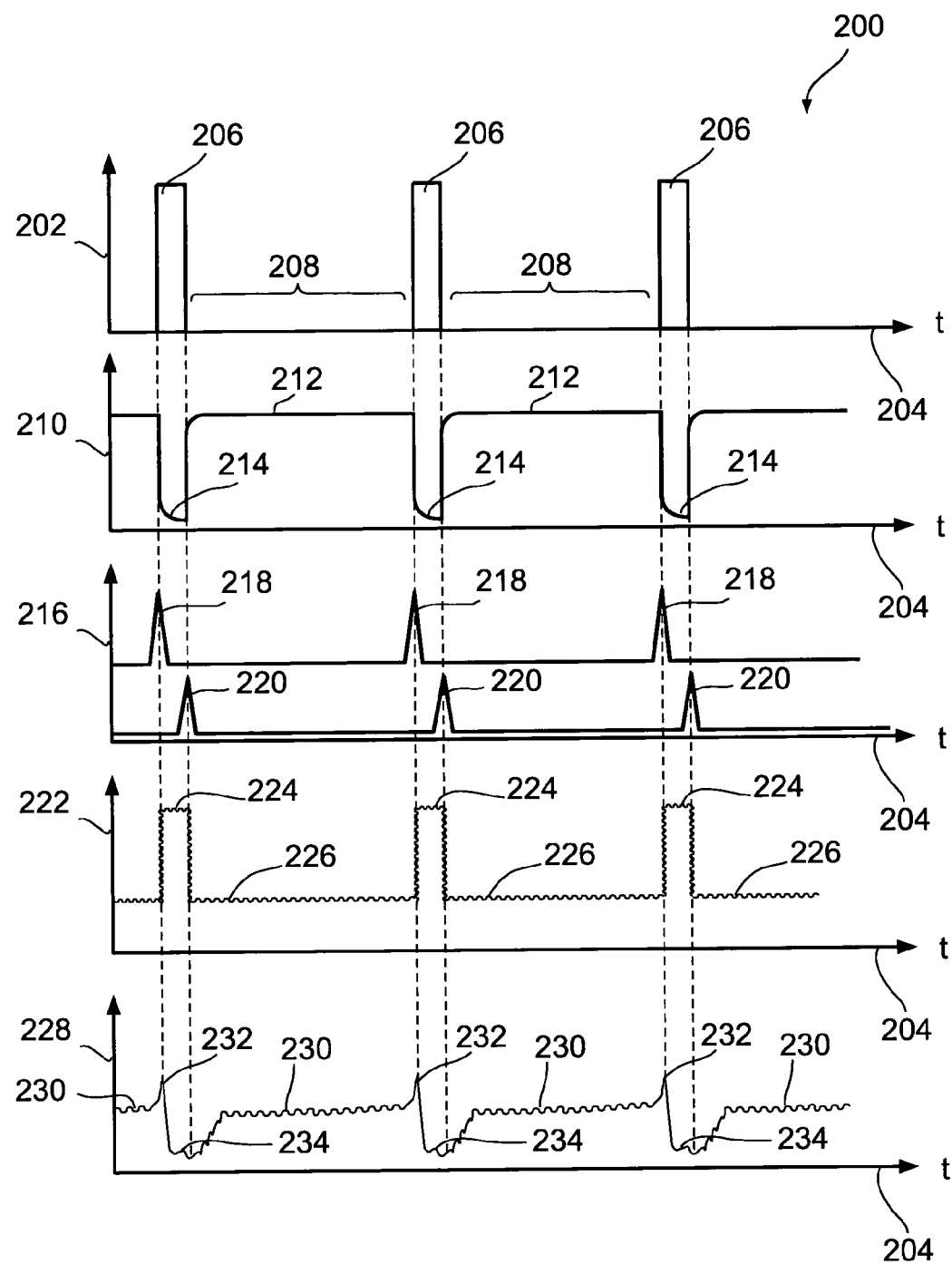
FIG. 2 is a schematic time plot of beam intensity during a few beam pulses, and corresponding plots of triggering signals, detector bias voltage, radiation received by the detector, and detector output, according to an exemplary embodiment of the invention.

FIG. 2 schematically shows a plot 200 of the beam intensity 202 as a function of time 204, showing pulses 206 and intervals 208 between pulses. Other quantities as a function of time, with the same time axis 204, are shown below the plot of beam intensity, for an embodiment of the invention in which the sensitivity of detector 118 and/or 124 is lowered during each beam pulse by decreasing the bias voltage of the detector.

Optionally, the duty cycle of beam source 108, the ratio of the interval of pulse 206 to the interval between pulses 208, is small, for example less than 20%, less than 10%, less than 5%, less than 2%, less than 1%, less than 0.5%, less than 0.2%, or less than 0.1%. For example, in a typical linac generating x-rays for radiation therapy, the pulse length may be 1 to 10 microseconds, or 0.1 to 1 microsecond, or 10 to 100 microseconds, or smaller or larger values, and the intervals between pulses may be 2.5 to 10 milliseconds, or 0.5 to 2.5 milliseconds, or 10 to 50 milliseconds, or smaller or larger values. In general, both the pulse time and the interval between pulses may be less than 100 milliseconds. The pulses in a linac are due to the fact that the microwaves responsible for accelerating electrons in the linac are generally produced by pulsed power from a discharging capacitor, which then takes a much longer time to charge up again, using a lower level of power from the power grid, than the time over which it discharges. In addition to this pulse structure, linac beams also have structure on a shorter timescale, on the order of a nanosecond, due to bunching of electrons in phase with the microwaves.

In the second plot from the top, the detector bias voltage 210 is shown schematically as a function of time 204. Many types of radiation detectors require outside power to detect radiation, which is supplied as a bias voltage, and these detectors cannot detect radiation at all if the bias voltage is too low. As used herein, "bias voltage" means any voltage applied to a detector, which affects the sensitivity of the detector. Examples include the voltage applied to the photomultiplier tube in a scintillation detector, the voltage supplied between the anode and cathode of a proportional counter, and the voltage applied to a semiconductor diode detector. During each pulse 206, the bias voltage is lowered to a level 214, so that the detector has decreased sensitivity to radiation. Optionally, level 214 is low enough so that the detector substantially does not detect radiation at all. During intervals 208 between pulses, the bias voltage is at a higher level 212, so that the detector is sensitive to radiation from the source, either an external source such as source 114 or an internal source such as source 120, that the detector is designed to be used with.

The third plot from the top schematically shows the amplitude 216 of trigger signals that trigger controller 126 to change the bias voltage. Trigger signals 218 at the beginning of each pulse trigger the controller to decrease the bias voltage of the detector, and trigger signals 220 at the end of each pulse trigger the controller to increase the bias voltage of the detector back to a higher value. In some embodiments of the invention, there is only one trigger signal per pulse, for example only at the beginning or only at the end of the pulse, and controller 126 calculates the beginning and/or end of the pulse from the single trigger signal, using a known pulse length and a known timing of the signal relative to the pulse. In some embodiments of the invention, the trigger signals are generated by a signal from sensor 128 which intercepts the beam, or intercepts scattered radiation from the beam, and measures its intensity as a function of time. For example, the trigger signals are optionally generated by taking a time derivative of the sensed beam intensity as a function of time, with oppositely biased diodes optionally used to separate "pulse start" trigger signals 218 from "pulse end" trigger signals 220, or the "pulse start" and "pulse end" signals may be distinguished by their polarity. Other analog and digital methods of generating trigger signals from sensor 128 will be apparent to one of skill in the art. Additionally or alternatively, information about the timing of the beginning and/or end of each beam pulse is obtained from beam source 108, or from a timing element that sends synchronized triggering signals both to the detector system and to beam source 108, to control the timing of the beam pulses. Additionally or alternatively, timing information about the beam pulses comes from one of the detectors. However, using a beam sensor, or using the beam source, or using a timing element, has the potential advantage that it may more accurately reflect the timing of the beam pulses than the detectors, which may be positioned and/or shielded to reduce their exposure to the beam radiation.

The fourth plot from the top in FIG. 2 schematically shows an intensity 222 of radiation received by detector 118 or 124, as a function of time. During each pulse 206, the direct and indirect interference radiation from beam source 108 dominates the signal from source 114 or source 120 that the detector is supposed to be measuring, raising it to a level 224 much greater than the lower level 226 during the intervals between pulses, which is due mostly to source 114 or 120. Even integrating over time, the contribution of the interference radiation may dominate the contribution from source 114 or source 120, or at least may be comparable to it. If the detector were equally sensitive to all radiation it receives, then the interference might substantially degrade images that are produced from data the detector generates, or substantially degrade the accuracy of tracking based on data that the detector generates.

The bottom plot in FIG. 2 schematically shows the actual response 228 of the detector to received radiation, as a function of time 204. In the intervals between pulses, when the detector has a high bias voltage 212, the detector response is at a level 230, due to the radiation from source 114 or 120 that the detector is designed to detect. At the beginning of each pulse, when the received radiation jumps up, the response may momentarily jump up to a still higher level 232, before the bias voltage has time to fall to level 214, because the rate at which the bias voltage can fall may be limited by the response time of the circuit, or there may be a short time delay before controller 126 receives a trigger signal indicating that the pulse has begun. This might be true, for example, if controller 126 relies on the detector itself to provide the trigger signal. Once the bias level falls sufficiently low that the sensitivity of the detector is substantially reduced, however, the response of the detector will fall to a level 234 which is optionally even lower than level 230, or at least is much lower, relative to level 230, than level 224 is relative to level 226. As a result, the integrated contribution of interference radiation from the beam to detector response 228 is less, sometimes much less, than the integrated contribution of radiation from source 114 or 120 to detector response 228. For example, the integrated contribution of interference radiation is at least 2 times less, or at least 5 times less, or at least 10 times less, or at least 20 times less, or at least 50 times less, than the integrated contribution from source 114 or 120. Images that are produced, or tracking that is done, using detector response 228 will then not be so degraded by interference radiation, and optionally are substantially not degraded at all.

It should be noted that the detector response 228 shown in FIG. 2 is a measure of radiation detected per unit time, integrated over a long enough time so that many photons (in the case of x-ray or gamma-ray sources) would be detected in an integration time, and there would be relatively small statistical fluctuations in the number of photons or the total energy of photons detected in an integration time. In some embodiments of the invention, the detector has a long enough integration time so that, at the level of radiation it is exposed to from source 114 or 120, it generates output data directly that look similar to detector response 228 in FIG. 2. This mode of operation of a detector is called "current mode," because the detector produces an output current that is proportional to the photon power received. In other embodiments of the invention, a shorter integration time is used, shorter than an average time between photons detected, and the direct output of the detector as a function of time looks like a series of individual narrow peaks, each corresponding to the detection of one photon, with the height of each peak proportional to the energy of the photon. This mode of operation of a detector is called "pulse mode." The detector may count the narrow peaks to produce a digital output signal proportional to the number of photons received per unit time. In this case, detector response 228 as plotted in FIG. 2 may be understood as a plot of an average number of photons per second, or an average energy of photons detected per second, found by integrating such a series of many individual peaks over time. These remarks apply as well to the plots of detector response as a function of time in FIGS. 3, 4, and 5.

In some embodiments of the invention, instead of or in addition to lowering the bias voltage of the detector during a beam pulse, controller 126 may decrease the voltage to digital counting circuitry of a detector operating in pulse mode, during the beam pulses, so that no photons are counted during the beam pulses, even though the detector is detecting photons. This option may be used as well in FIG. 6.

In some embodiments of the invention, rather than lowering the bias voltage, or decreasing the voltage to digital counting circuitry, only during the beam pulses, controller 126 lowers the bias voltage, or the voltage to the counting circuitry, for longer periods of time each including the time of a beam pulse. These longer periods of time may extend to several times as long as the decay time of the detector response, following the beam pulse, even if the decay time is comparable to or longer than the time of each beam pulse. In such a case, keeping the detector insensitive to radiation for at least a few times the decay time prevents the detector from producing a delayed high level response to the radiation received directly or indirectly from the beam, after the beam pulse. This option may be used as well for FIG. 6. However, optionally the detector is insensitive to radiation for a time much shorter than the interval between pulses. This allows the detector to detect radiation most of the time, and to detect most of the radiation it receives from the monitoring source.

Figure 3:
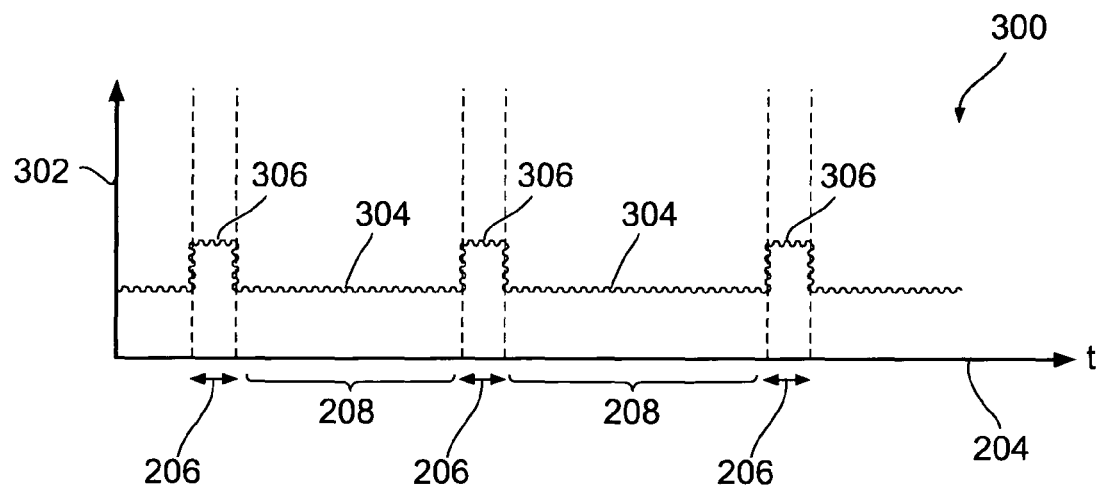
FIG. 3 is a schematic time plot of detector output for a saturating non-paralyzable detector, for the same beam intensity and received radiation as functions of time shown in FIG. 2, according to another exemplary embodiment of the invention.

FIG. 3 schematically shows a plot 300 of the detector response 302 as a function of time 204, for the same arrangement of beam pulses as a function of time, and received radiation as a function of time, as is shown in FIG. 2. The detector in FIG. 3 does not have a changing bias voltage, but has a relatively low saturation level, lower than the high level of received radiation during the pulses, but higher than the level of received radiation between pulses. Photon detectors generally operate by discharging a charge, typically proportional to the photon energy, whenever they detect a photon, which reduces the bias voltage until the charge can be replaced. If the rate at which the charge can be replaced is limited, for example by an impedance in series with the source of the bias voltage, then the response of the detector will saturate at a current equal to the maximum current with which the detector can be recharged. In FIG. 3, the response is at a level 304, below saturation, in the intervals 208 between beam pulses, and is at a somewhat higher level 306, at the saturation level, during beam pulses 206, when the amount of radiation received by the detector is much greater. The integrated detector response during the beam pulses, however, is small compared to the integrated detector response between beam pulses, because the beam has a small duty cycle of pulses. As a result, interference from the beam contributes only a small amount, for example less than 20%, 10%, 5%, 2% or 1%, to the integrated detector response, and to the data record based on it, which is used for imaging or tracking.

Figure 4:
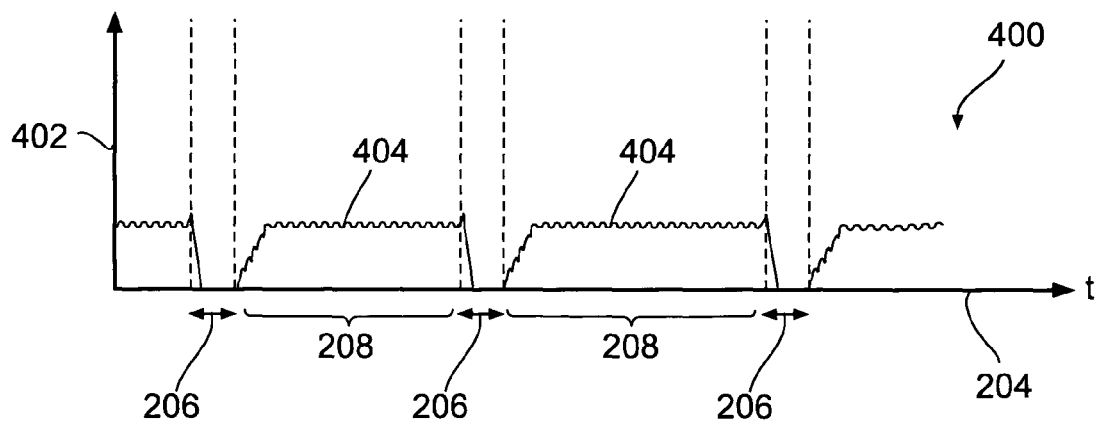
FIG. 4 is a schematic time plot of detector output for a saturating paralyzable detector, for the same beam intensity and received radiation as functions of time shown in FIG. 2, according to another exemplary embodiment of the invention.

The detector response shown in FIG. 3 is the response for a non-paralyzing detector. Such a detector will respond at the saturation level when it receives radiation above the saturation level, because radiation received during the "dead time," when the detector has not yet recovered its bias voltage, do not prolong the dead time. FIG. 4 shows a plot 400 of the response 402 of a paralyzing detector as a function of time 204, for the same beam intensity, and received radiation, as a function of time, as shown in FIG. 2. A paralyzing detector does not respond at all if it receives radiation above the saturation level, since radiation received during the dead time can restart the dead time, prolonging recovery. In FIG. 4, the detector response 402 is at a level 404, below the saturation level, during the intervals 208 between pulses, but during the pulses 206 the detector response is zero. Due to any finite rise and fall times of the beam pulses, as well as the finite decay time of the detector response, the detector may rise somewhat at the beginning of each pulse, before falling to zero, and may take some time to return to level 404 after the beam pulse, as shown in FIG. 4. However, if the saturation level is not too far above level 404, then the small rise at the beginning of each pulse will not contribute very much to the integrated detector response. And if the decay time and pulse length are short compared to the interval between pulses, then the detector will not miss more than a small fraction of the radiation in the interval between pulses, due to the finite rise time in the detector response after the pulse.

It should be noted that "paralyzing" and "non-paralyzing" detectors are abstract models of detector behavior, and in practice most types of detectors fall somewhere in between these two extremes.

Figure 5:
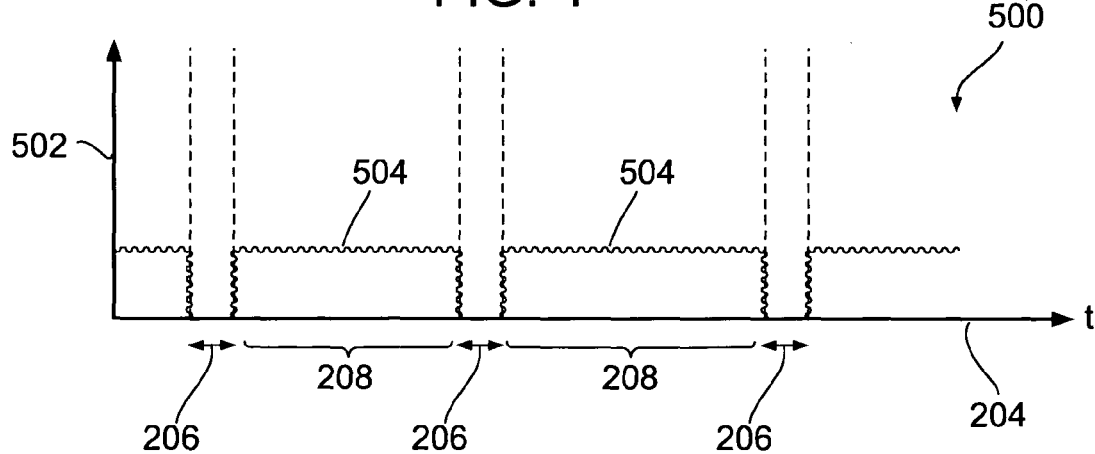
FIG. 5 is a schematic time plot of radiation intensity in the final data record, for the same beam intensity and received radiation as functions of time shown in FIG. 2, according to another exemplary embodiment of the invention.

FIG. 5 schematically shows a plot 500 of a data record of a detector response 502 as a function of time 204, for the same beam pulses 206, and intervals 208 between pulses, as shown in FIG. 2, and for the same level 222 of radiation received by the detector as shown in FIG. 2. In the case shown in FIG. 5, the detector may fully respond to of the radiation it receives. However, the radiation received during beam pulses is not written to the data record of the detector response, or is removed from the data record. The data record shows a level 504 during intervals 208 between pulses, but a level of zero during pulses 206. This may be done, as described above, by having controller 126 reduce the voltage to counting circuitry of the detector, during pulses, so any photons detected during beam pulses are not counted. Alternatively, controller 126 may use software which sets the data record to zero for pulse times 206, after a data record is written which includes information about the time dependence of the intensity of radiation detected in each section of the detector. The times 206 of the beam pulses may be identified by using information from beam source 108, or sensor 128, or the times of the beam pulses may be identified because they have high levels of radiation detected by the detector.

Figure 6:
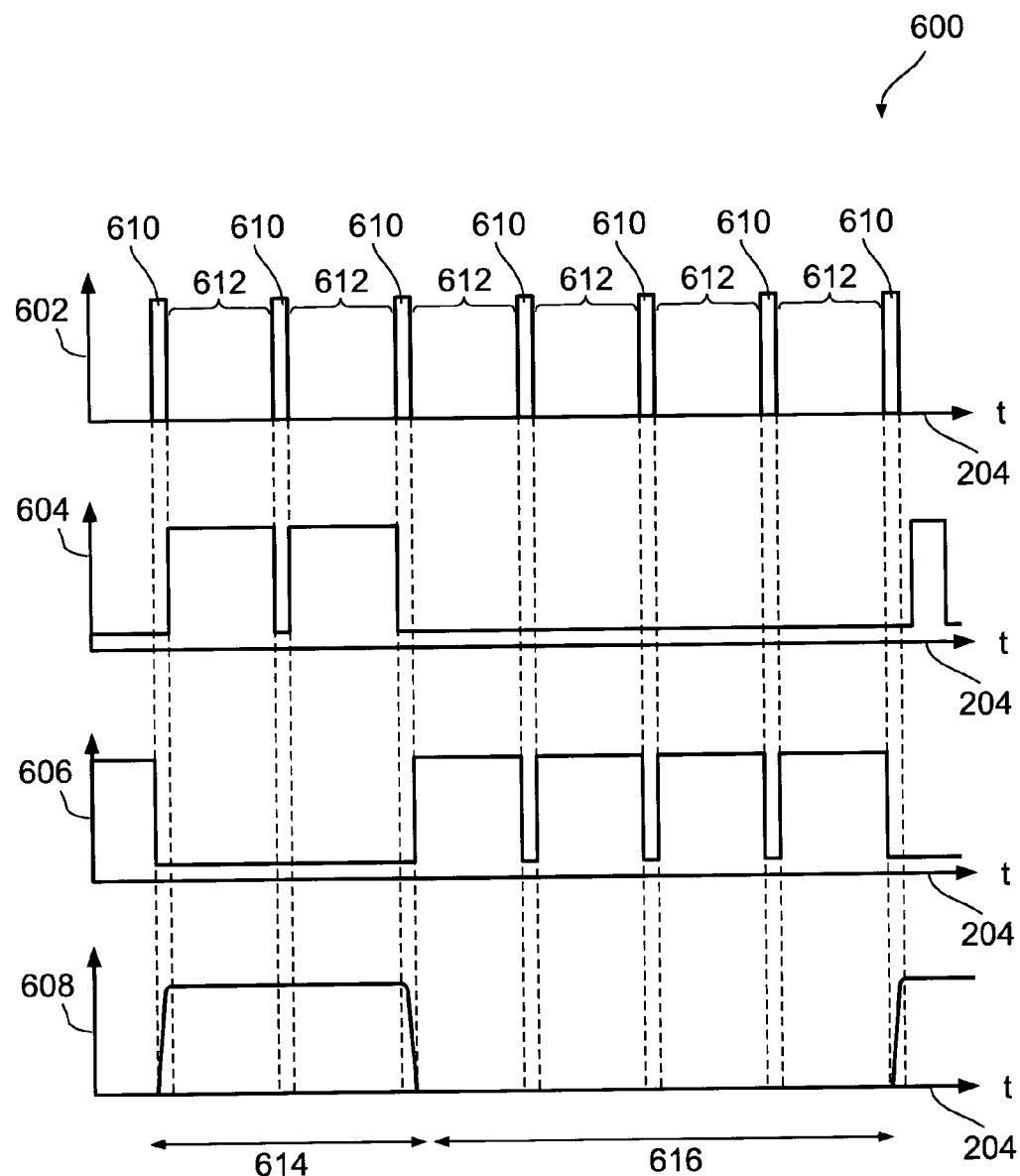
FIG. 6 is a schematic time plot of beam intensity, intensity of an imaging x-ray source, and bias voltages for an imaging x-ray detector and a gamma imaging or tracking detector, according to another exemplary embodiment of the invention.

FIG. 6 schematically shows plots 600 of beam intensity 602 and other quantities as functions of time 204, including a bias voltage 604 for detector 118 detecting radiation from external source 114, a bias voltage 606 for detector 124 detecting radiation from source 120 inside the patient's body, and an intensity 608 of radiation from source 114. As in FIGS. 2-5, the beam intensity has pulse times 610 separated by intervals 612 between pulses. Also as in FIG. 2, the bias voltages of both detector 118 and detector 124 are lowered during the beam pulse times 610, optionally using any of the methods for doing this described above for FIG. 2. But in FIG. 6, unlike in FIG. 2, there is a time division between a period 614 when detector 118 operates, and a period 616 when detector 124 operates, in order to avoid interference from radiation source 114 on detector 124. Radiation source 114 produces radiation during period 614, but does not produce radiation, or produces radiation at a low level, during period 616. The time-averaged level of radiation produced by source 114 may be set by a trade-off between quality of images produced by detector 118, and possible dangers of radiation exposure to the patient. If so, then the same optimal average level of radiation from source 114 may be achieved to using a higher level of radiation with a lower duty cycle. It may be advantageous to use a relatively low duty cycle for radiation source 114 and detector 118, well below 50%, and to use a relatively high duty cycle for detector 124, not too far below 100%, because using a lower duty cycle will reduce the quality of imaging or tracking by detector 124, while using a lower duty cycle will not adversely affect the quality of imaging by detector 118. However any duty cycles may be used. Although source 120, inside the body, is not turned off during period 614 when detector 118 is on, any interference from source 120 can be reduced by using a lower duty cycle and correspondingly higher intensity for source 114. In any case, source 120, being implanted inside the body and producing radiation isotropically, is likely to produce very little interference in detector 118, compared to the radiation received from source 114, which is directed at detector 118, and which can safely be of higher intensity than radiation source 120 because it is only used for a limited time.

Periods 614 and 616 need not be longer than intervals 612 between beam pulses, as shown in FIG. 6, but could be shorter than intervals 612, and each interval 612 could, for example, be divided into an interval 614 and an interval 616. Periods 614 and 616 may also be much longer than intervals 612, for example between 10 milliseconds and 100 milliseconds, or longer than 100 milliseconds. However, it may be advantageous not to make these periods so long that the patient, or a part of the patient's body, could move significantly, for example a distance comparable to the diameter of the beam, within one of these periods, because then the detector that is not operating will not be able to detect the motion.

It should be noted that, for any of the embodiments in which controller 126 actively controls the detector, by changing its bias voltage, or affecting its ability to record data, or in which controller 126 fails to record data or removes data based on the timing of the detection of the radiation, the corresponding control circuitry and/or timing circuitry in controller 126 is optionally fast enough to respond in much less than the interval between pulses, and optionally in less than a pulse length. If the detector system, in these embodiments, is adapted to monitor a given radiation treatment system, this means that it has control and/or timing electronics with the appropriate speed, depending on the pulse length and interval between pulses of that radiation treatment system. But this need not be true in embodiments where saturation of the detector is used to reduce detection of radiation during beam pulses, although in those embodiments it is still advantageous for the detector to have a short enough decay time.

For example, the detector system is capable of selectively excluding data for radiation received over a time period as short as 100 milliseconds, or 10 milliseconds, or 1 millisecond, or 100 microseconds; or 10 microseconds, as opposed to radiation received outside this time period. In some embodiments of the invention, this is accomplished by actively controlling the detector to be less sensitive or not to record data during that time period, or by timing the radiation received and removing data corresponding to that time period. In these embodiments, the control circuitry, including the timing circuitry, is fast enough to accomplish this. In other embodiments of the invention, this is accomplished by having a detector that saturates at a low enough level. In all these embodiments, the detector optionally has a decay time shorter than the time period during which radiation is excluded.

Optionally, in any of the radiation treatment systems described above, the decreased contribution to the detector data record of radiation during the beam pulses is such that this contribution of the direct and indirect radiation from the beam pulses is at least 2 times less, or at least 5 times less, or at least 10 times less, or at least 20 times less, or at least 50 times less, than the contribution that radiation from the beam pulses make to the total radiation received by the detector, for at least one detector used in an imaging or tracking system. Optionally, the contribution to the detector data record of radiation during the beam pulses is sufficiently low that interference from beam radiation is at least a factor of 2 less, or at least a factor of 5 less, or at least a factor of 10 less, or at least a factor of 20 less, or at least a factor of 50 less, than the contribution of radiation from the radiation source, external or internal, that is designed to be used with that detector for imaging or tracking. Optionally, any remaining interference from beam radiation is sufficiently small that it substantially does not affect the quality of images produced, for example the SNR, or the accuracy of tracking, for a given acquisition time.

In some implementations, the invention can be used with existing beam therapy systems, without the need to modify the beam source.

In some embodiments of the invention, imaging with an external radiation source 114, and imaging or tracking with an internal radiation source 120, are used on a patient, even without using a beam for radiation treatment. In these embodiments, periods 614 when source 114 and corresponding detector 118 are operating, are alternated with periods 616 when source 114 and detector 118 are not operating, while detector 124 for source 120 is operating. This reduces or eliminates interference of source 114 on detector 124, and, for a given average power of source 114, reduces interference of source 120 on detector 118. For the reasons given above, it may be advantageous to make periods 614 much shorter than periods 616.

Although the embodiments of the invention shown in FIGS. 1-6 all involve patients receiving medical treatment with the radiation beam, similar methods are optionally used in industrial processes where an inanimate body is being treated by a radiation beam, and is being monitored by an imaging or tracking system using another source of radiation, and a radiation detector, to avoid or reduce interference of the beam on the detector.

It is expected that during the life of a patent maturing from this application many relevant radiation beams and detectors will be developed and the scope of the terms radiation beam and radiation detector is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A detector system adapted for monitoring a radiation treatment system comprising a pulsed beam radiation source for treating a body with a therapy beam having a given beam intensity and a given beam configuration, with pulse times and intervals between pulse times less than 100 milliseconds, the detector system adapted to use at least one monitoring radiation source located inside the body, the monitoring radiation source and the pulsed beam radiation source together producing interference radiation, the detector system comprising;
a detector designed to detect radiation from the monitoring radiation source; and
control circuitry that generates a data record of radiation received by the detector, to provide information about the body;
wherein the detector is subject to the interference radiation; and
wherein, during operation of the detector, the data record is designed to selectively exclude data of interference radiation received by the detector during the pulse times.

2. The detector system of claim 1, wherein the control circuitry is configured to control a relative sensitivity of the detector during at least the pulse times, and the control circuitry is configured to lower the relative sensitivity of the detector during the pulse times in comparison to a sensitivity of the detector in the intervals between the pulse times.

3. The detector system of claim 2, wherein the relative sensitivity of the detector is responsive to a bias voltage, and the control circuitry is configured to vary the bias voltage.

4. The detector system of according of claim 2 further comprising: a triggering element configured to signal the pulse times to the control circuitry.

5. The detector system of claim 4, wherein one of a set of: the pulsed beam radiation source and a timing element comprises:
the triggering element, and
wherein the timing element is configured to control, at least, the pulse times of the pulsed beam radiation source.

6. The detector system of claim 4, wherein a sensor comprises the triggering element; and
wherein the sensor is configured to sense when the pulsed beam radiation source produces a pulse.

7. The detector system of claim 6, wherein the sensor is the detector.

8. The detector system of claim 1, wherein the control circuitry is configured to selectively avoid adding data of interference radiation detected by the detector during the pulse times to the data record.

9. The detector system of claim 1, wherein the control circuitry is configured to selectively remove data of interference radiation detected by the detector during the pulse times from the data record.

10. The detector system of claim 1, wherein the detector is configured to saturate in response to a level of interference radiation received during the pulse times for the given beam intensity and the given beam configuration, and wherein the detector is configured to avoid saturating in response to a level of radiation received from the monitoring radiation source during the intervals between the pulse times.

11. The detector system of claim 1, wherein the detector is a scintillation detector with decay time shorter than the intervals between the pulse times.

12. The detector system of claim 1, wherein a time-averaged relative contribution of the interference radiation to the data record is less, by at least a factor of 5, than a time-averaged relative contribution of the interference radiation to the radiation received by the detector, when the pulsed beam radiation source is operating at the given beam intensity and the given beam configuration.

13. The detector system of claim 1, wherein the interference radiation contributes to the data record less than 20% of a contribution to the data record from radiation from the monitoring radiation source, averaged over any time interval that includes many pulse times, when the pulsed beam radiation source is operating at the given beam intensity and the given beam configuration.

14. The detector system of claim 1, wherein the radiation treatment system is a radiation therapy system and the given beam intensity is at least 1 centiGray per second, and the detector system is configured to locate a beam therapy target inside the body to within 2 mm in an acquisition time of less than 2 seconds, using one of a set of: an internal monitoring radiation source of less than 1 milliCurie and an external x-ray monitoring radiation source of less than 20 centiGray per acquisition time.

15. The detector system of claim 14, wherein the data record provides information on at least one of a set of: motion of the body, position of the body, and motion and position of at least one portion of the body; and
wherein information on one of the set of the motion of the body, the position of the body, and the motion and position of at least one portion of the body includes at least location information relative to a real time location of a portion of the therapy beam during the pulse times.

16. The detector system of claim 14, wherein the pulsed beam radiation source comprises a linac beam source.

17. The detector system of claim 16, wherein the linac beam source comprises an x-ray beam source.

18. The detector system of claim 14, wherein the pulsed beam radiation source comprises an ion beam source.

19. The detector system of claim 1 comprising an x-ray imaging system, wherein the monitoring radiation source comprises an x-ray source.

20. The detector system of claim 19 comprising a CT system.

21. The detector system of claim 1 comprising a radioactive tracking system configured to use the monitoring radiation source, wherein the monitoring radiation source comprises a radioactive source.

22. The detector system of claim 1 comprising a gamma imaging system, wherein the gamma imaging system is configured to use the monitoring radiation source, and wherein the monitoring radiation source comprises a radioactive material.

23. The detector system of claim 1, wherein the control circuitry is adapted to determine a difference between a position of a treatment target in the body and a planned position of the treatment target with respect to the given beam configuration, and to adjust in response to the difference at least one of: the given beam configuration and the given beam intensity.

24. The detector system of claim 1, wherein during a time period shorter than 100 milliseconds, the data record is capable of selectively excluding data of interference radiation received by the detector during the pulse times based on at least one of the following conditions: the control circuitry is configured to operate sufficiently fast enough and the detector exhibits a sufficiently fast decay time.

25. The detector system of claim 24, wherein the time period is shorter than 10 milliseconds.

26. A method of monitoring a body in real time while the body is being treated by a pulsed beam of treatment radiation, with pulse times and intervals between pulse times shorter than 100 milliseconds, the method comprising:
- receiving monitoring radiation from a source inside the body, wherein the monitoring radiation passes through at least part of the body;
- receiving at least some interfering radiation from the pulsed beam of treatment radiation;
- recording, in a data record, data of detection of the monitoring radiation; and
- using the data record to monitor the body in real time during operation of the pulsed beam of treatment radiation;
- wherein receiving at least some interfering radiation from the pulsed beam of treatment radiation and recording, in a data record, data of detection of the monitoring radiation selectively excludes from the data record data of radiation received during the pulse times.

27. The method of claim 26, wherein using the data record to monitor comprises reconstructing images.

28. The method of claim 26, wherein using the data record to monitor comprises tracking a location of the source.

29. The method of claim 26, wherein the body is a patient's body, and the pulsed beam of treatment radiation is designed to provide radiation therapy for the patient's body.

30. The method of claim 26, wherein recording, in a data record, data of detection of the monitoring radiation comprises at least one of: selectively avoiding recording to the data record, and selectively removing from the data record, data of detection of the interfering radiation received during the pulse times.

31. The method of claim 26 further comprising: lowering a detection sensitivity to radiation during the pulse times, and raising the detection sensitivity during intervals between the pulse times.

32. The method of claim 31 further comprising: receiving triggering signals indicating the beginning and end of each pulse time, wherein lowering and raising the detection sensitivity is done in response to the triggering signals.

33. The method of claim 26, wherein recording, in a data record, data of detection of the monitoring radiation comprises detecting with a saturation level that is both lower than a level of interfering radiation received during the pulse times and higher than a level of radiation received during the intervals between the pulse times.

34. The method of claim 26, wherein using the data record to monitor the body in real time comprises:
- determining a difference between a position of a beam therapy target in the body, and a planned position with respect to a location of the pulsed beam of treatment radiation; and
- adjusting at least one of: the location of the pulsed beam of treatment radiation and reducing a power of the pulsed beam of treatment radiation, in response to the difference.

\* \* \* \* \*